US00PP09014P

United States Patent [19]

Tachibana et al.

[11] Patent Number: Plant 9,014

[45] Date of Patent: Dec. 13, 1994

[54] VERBENA PLANT—'SUNMAREF TP-P'

[75] Inventors: Ryuichi Tachibana, Yamato; Yuji Tamura, Kofu; Ushio Sakazaki, Hikone, all of Japan

[73] Assignee: Suntory Limited, Osaka, Japan

[21] Appl. No.: 226,115

[22] Filed: Apr. 8, 1994

Related U.S. Application Data

[63] Continuation of Ser. No. 100,253, Aug. 2, 1993, abandoned.

[51] Int. Cl.[5] ..... A01H 5/00

[52] U.S. Cl. ..... Plt./87

[58] Field of Search ..... Plt. 87

U.S. PATENT DOCUMENTS

PLT 6963 8/1989 Egger ..... PLT/87

PLT 7439 2/1991 Egger ..... PLT/87

*Primary Examiner*—James R. Feyrer

*Attorney, Agent, or Firm*—Burns, Doane, Swecker & Mathis

[57] ABSTRACT

Disclosed herein is a spreading growth habit type verbena plant having long stems. The plant has abundant branching and each node in the branches contacting the ground commonly forming deep-spreading roots. The plant forms many flowers from on ascending spikes with and a great profusion of blooms. The flowers exhibit petals having a deep purplish pink coloration, with a small deep strong purplish red eye. The plant is highly resistant to heat, cold, rain, diseases, and pests.

4 Drawing Sheets

This application is a continuation of application Ser. No. 08/100,253, filed Aug. 2, 1993, now abandoned.

BACKGROUND OF THE VARIETY

The present invention relates to a new and distinct variety of Verbena obtained from the crossing of one verbena plant (♀) which was selected from a crossing of 'Rainbowcarpet Brightpurple' (♀) and a wild type of verbena plant (♂) native to Brazil, and 'Rainbowcarpet Red' (♂). The 'Rainbowcarpet Brightpurple' and 'Rainbowcarpet Red' parents are botanically known as Verbena×hybrida Voss.

Verbena of the presently commercialized 'Rainbowcarpet' series is a semi-erect growth habit having medium stems, medium branching, and a scant number of flowers in ascending spikes, and has moderate tolerance to heat and cold. Accordingly, this invention was aimed at obtaining a new variety having a spreading growth habit, abundant branching, many flowers, high tolerances to heat and cold, and resistances to diseases and pests, which are superior to those of said 'Rainbowcarpet' series, and also having a pink flower color.

A crossing of 'Rainbowcarpet Brightpurple' as the female parent and a wild type of verbena plant native to Brazil as the pollen parent was practiced, in 1988, at the Plant Biotechnology Laboratory, Institute for Fundamental Research of SUNTORY Ltd., residing at 2913-1 Torihara, Hakushu-cho, Kitakoma-gun, Yamanashi-ken, Japan. From this crossing, 75 seedlings were obtained in the spring of 1988, then a crossing of the 20 seedings which were selected from obtained 75 seedings as the female parent and 'Rainbowcarpet Red' obtained from TAKII SEED & SEEDLING Corp., as the pollen parent was practiced at the same place. From this crossing 60 seedlings were obtained in the summer of 1988, from which 3 seedlings were selected, propagated by cutting, and then grown as a trial by flower bedding and potting for the spring of 1989. Only one of the 3 resulting plants was selected. The botanical characteristics of the finally-selected plant were then examined, using a similar varieties, 'Rainbowcarpet Rose' and 'Rainbowcarpet Brightpurple', for comparison, from the spring of 1990. As a result, it was concluded that this verbena plant is distinguishable from any other variety whose existence is known to use, and this new variety of verbena plant was named 'Sunmaref TP-P' (Tapien Pink ®).

In the following description, the color-coding is in accordance with the Horticultural Color Chart of The Royal Horticultural Society, London, England (R.H.S. Color Chart), and the Inter-Society Color Council-Nation Bureau of Standards Color Name (ISCC-NBS Color Name). A color chart based on The Japan Color Standard for Horticultural Plants (J.H.S. Color Chart) is also added for reference.

'Rainbowcarpet Brightpurple' used as the female parent in the obtaining of one verbena plant used as the female parent in the breeding this new variety 'Sunmaref TP-P' is one of the 'Rainbowcarpet' series bred by the TAKII SEED & SEEDLING Corp., Japan. The 'Rainbowcarpet' series includes 'Rainbowcarpet Rose', 'Rainbowcarpet White', and the like. The main botanical characteristics of 'Rainbowcarpet Brightpurple' are as follows.

Plant:

*Growth habit.*—Semi-erect.

*Plant height.*—25–30 cm.

*Plant extension.*—30–35 cm.

*Blooming period.*—Late April to November.

Stem:

*Diameter.*—2–3 mm.

*Anthocyanin pigmentation.*—Absent.

*Branching.*—Medium.

*Pubescence.*—Scant.

*Length of internode.*—35–40 mm.

Leaf:

*Phyllotaxis.*—Opposite.

*Shape of blade.*—Broadly ovate.

*Length.*—20–25 mm.

*Width.*—15–20 mm.

*Depth of incision.*—Deep. Color.—Deep yellow green (R.H.S. 141A, J.H.S. 3706).

Pubescence.—Few.

Flower:

*Direction.*—Ascending.

*Outward curvatuve of petal.*—Slightly curved.

*Diameter.*—10–15 mm.

*Length.*—13–15 mm.
*Color.*—Vivid purple (R.H.S. 82A, J.H.S. 8606).
*Color intensity.*—Absent.
*Overlapping of petals.*—Separate.
*Spike.*—25–30 mm in length; and 30–35 mm in diameter.
*Calyx.*—0.5–1.0 cm.
*Anthocyanin pigmentation of calyx limb.*—Present.
*Peduncle.*—Less then 2 mm in diameter; and 6.0–8.0 cm in length.
*Number of flowers.*—Few (9±2).
*Productive organs.*—1 pistil and 5 stamens.
*Physiological and ecological characteristics.*—Moderate resistances to pests and diseases, and moderate tolerances to cold and heat.

The plant used as the pollen parent in the obtaining of the female parent in the breeding of this new variety 'Sunmaref TP-P' is a wild type of verbena plant native to South Brazil and this wild type of plant is presently maintained at the Plant Biotechnology Laboratory of SUNTORY Ltd. The main botanical characteristics of the pollen parent are as follows.

Plant:
*Growth habit.*—Spreading.
*Plant height.*—10–15 cm.
*Plant extension.*—80–100 cm.
*Blooming period.*—Late April to November.
Stem:
*Extending.*—40–50 cm.
*Diameter.*—2–3 mm.
*Anthocyanin pigmentation.*—Absent.
*Branching.*—Abundant.
*Pubescence.*—Medium.
*Length of internode.*—20–30 mm.
Leaf:
*Phyllotaxis.*—Opposite.
*Shape of blade.*—Ovate.
*Length.*—15–20 mm.
*Width.*—10–15 mm.
*Depth of incision.*—Deep.
*Color.*—Deep yellow green (R.H.S. 141A, J.H.S. 3706).
*Pubescence.*—Medium.
Flower:
*Direction.*—Ascending.
*Outward curvature of petal.*—Slightly curved.
*Diameter.*—10–15 mm.
*Length.*—12–15 mm.
*Color.*—Brilliant purple (R.H.S. 86C, J.H.S. 8604).
*Color intensity.*—Absent.
*Overlapping of petals.*—Separate.
*Spike.*—30–40 mm in length; and 35–40 mm in diameter.
*Calyx.*—0.5–1.0 cm in length.
*Anthocyanin pigmentation of calyx limb.*—Absent.
*Peduncle.*—1–2 mm in thickness; and 30–50 mm in length.
*Number of flowers.*—Medium (10±2).
*Productive organs.*—1 pistil and 5 stamens.
*Physiological and ecological characteristics.*—High resistances to disease and pests, and high tolerances to heat and cold.

'Rainbowcarpet Red' used as the pollen parent used in the breeding of this new variety 'Sunmaref TP-P' is one of the 'Rainbowcarpet' series bred by the TAKII SEED & SEEDLING Corp., Japan. The main botanical characteristics of the 'Rainbowcarpet Red' are as follows.

Plant:
*Growth habit.*—Semi-erect.
*Plant height.*—25–30 cm.
*Plant extension.*—20–25 cm.
*Blooming period.*—Late April to November.
Stem:
*Diameter.*—2–3 mm.
*Anthocyanin pigmentation.*—Absent.
*Branching.*—Medium.
*Pubescence.*—Scant.
*Length of internode.*—35–40 mm.
Leaf:
*Phyllotaxis.*—Opposite.
*Shape of blade.*—Broadly ovate.
*Length.*—20–25 mm.
*Width.*—15–20 mm.
*Depth of incision.*—Shallow.
*Color.*—Deep yellow green (R.H.S. 141A, J.H.S. 3706).
*Pubescence.*—Few.
Flower:
*Direction.*—Ascending.
*Outward curvature of petal.*—Slightly curved.
*Diameter.*—10–15 mm.
*Height.*—13–15 mm.
*Color.*—Vivid red (R.H.S. 42A, J.H.S. 0707).
*Color intensity.*—Absent.
*Overlapping of petals.*—Separate.
*Spike.*—25–30 mm in length; and 30–35 mm in diameter.
*Calyx.*—0.5–1.0 cm in length.
*Anthocyanin pigmentation of calyx limb.*—Present.
*Peduncle.*—Less than 2 mm in diameter; and 6.0–8.0 cm in length.
*Number of flowers.*—Medium (10±2).
*Productive organs.*—1 pistil and 5 stamens.
*Physiological and ecological characteristics.*—Moderate resistances to diseases and pests, and moderate tolerances to cold and heat.

This new variety of verbena plant, 'Sunmaref TP-P' was asexually reproduced by cuttings at the aforementioned the Plant Biotechnology Laboratory, Institute for Fundamental Research of SUNTORY Ltd., residing at 2931-1 Torihara, Hakushu-cho, Kitakoma-gun, Yamanashi-ken, Japan, and the homogeneity and stability thereof were confirmed.

SUMMARY OF THE VARIETY

The new variety of verbena plant has a spreading growth habit with very long stems and a low one in height, and the spreading area of plant is broad and thus is very different from the similar varieties, 'Rainbowcarpet Rose', and 'Rainbowcarpet Brightpurple'. The plant has abundant branching and numerous flowers in ascending spikes, and a great profusion of blooms which are clearly distinguishable from the similar varieties, 'Rainbowcarpet Rose', and 'Rainbowcarpet Brightpurple', and the whole bush remains in bloom for a considerable period of time, that is longer than the blooming period of 'Rainbowcarpet Rose'. The length of internode of the new variety is longer than that of similar varieties, and each node contacting the ground commonly forms deep-spreading roots, that attach the plant well to the ground. The flowers have petals having a deep purplish pink color, with a small more strongly purplish red eye. The plant is highly resistant to cold, heat, deseases, and pests.

DESCRIPTION OF THE VARIETY

Figure 1:
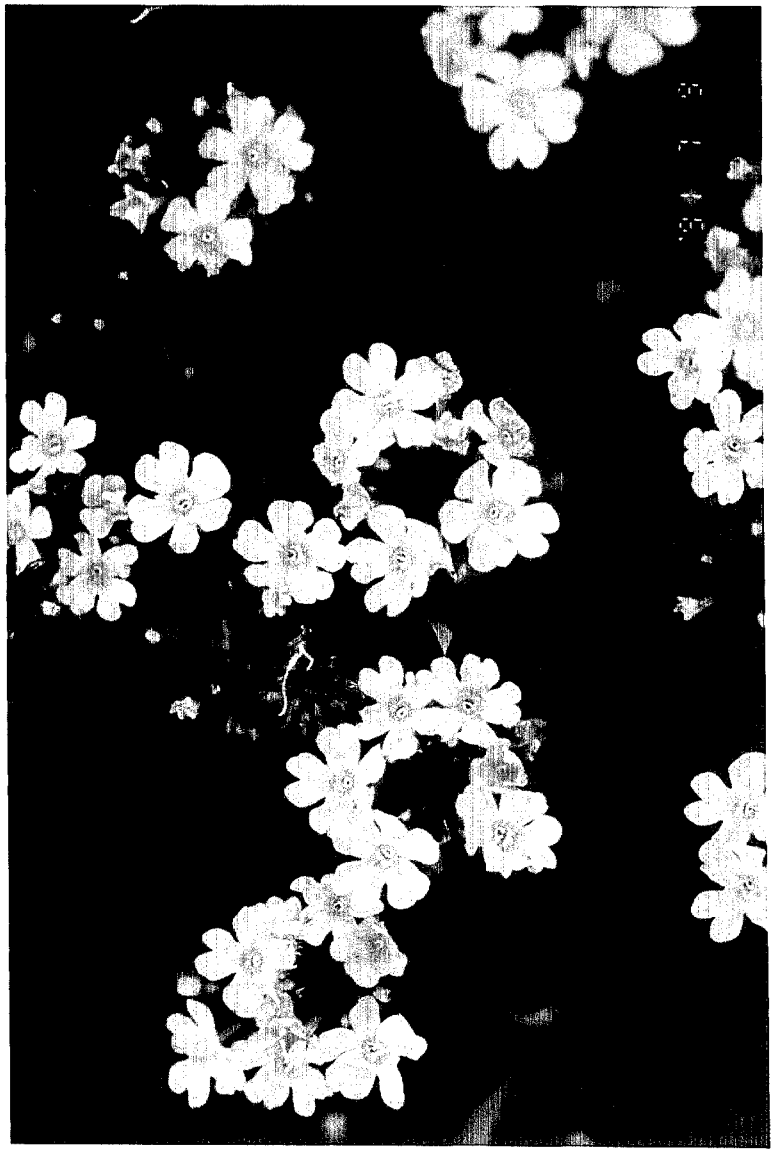
FIG. 1 is photograph of flowers of the new variety of verbena plant.
Figure 2:
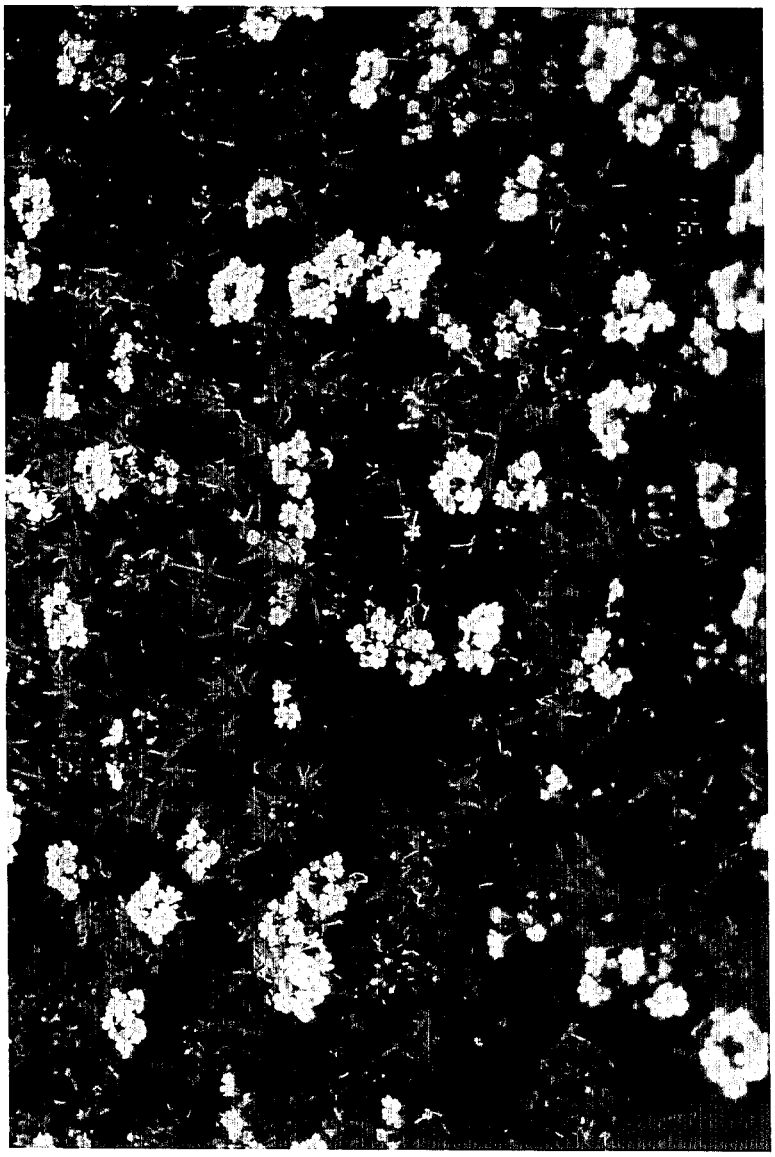
FIG. 2 is a photograph giving a partial view of the new variety of verbena plant planted in a flower bed.
Figure 3:
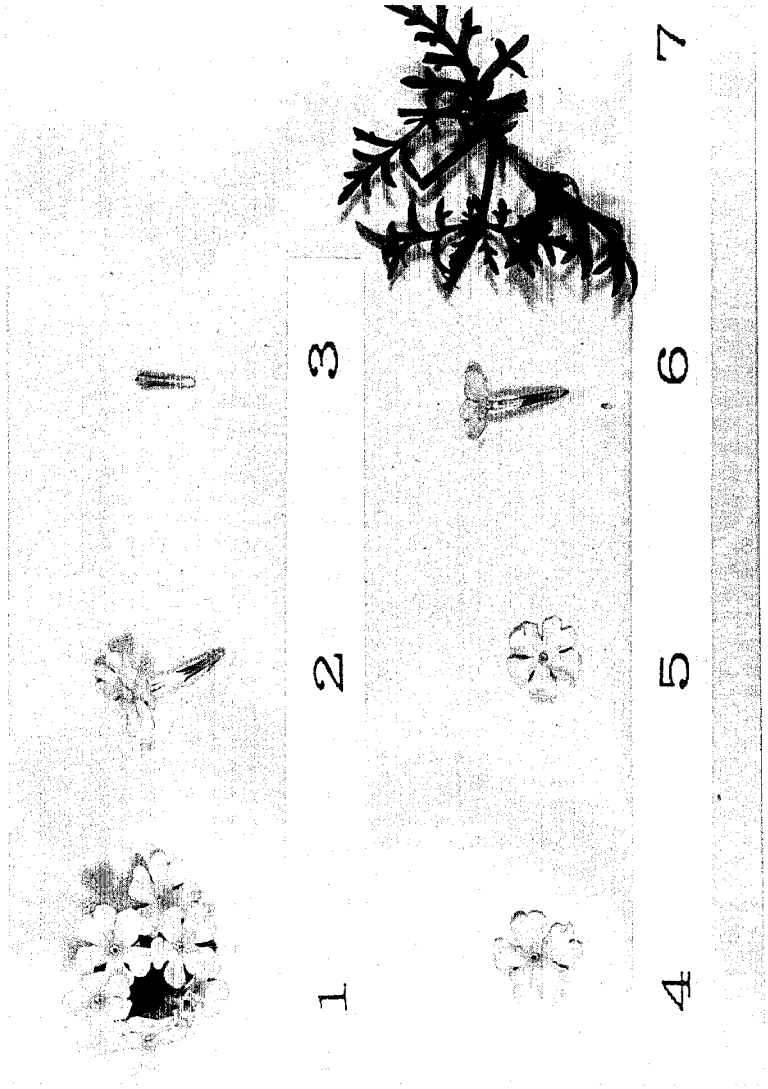
FIG. 3 is a photograph showing, in numerical order, a cluster (1), a flower (2), a bud (3), a surface view of the flower (4), a rear view of the flower (5), a cross-sectional view of the flower (6), and branch (7), of the new variety of verbena plant.
Figure 4:
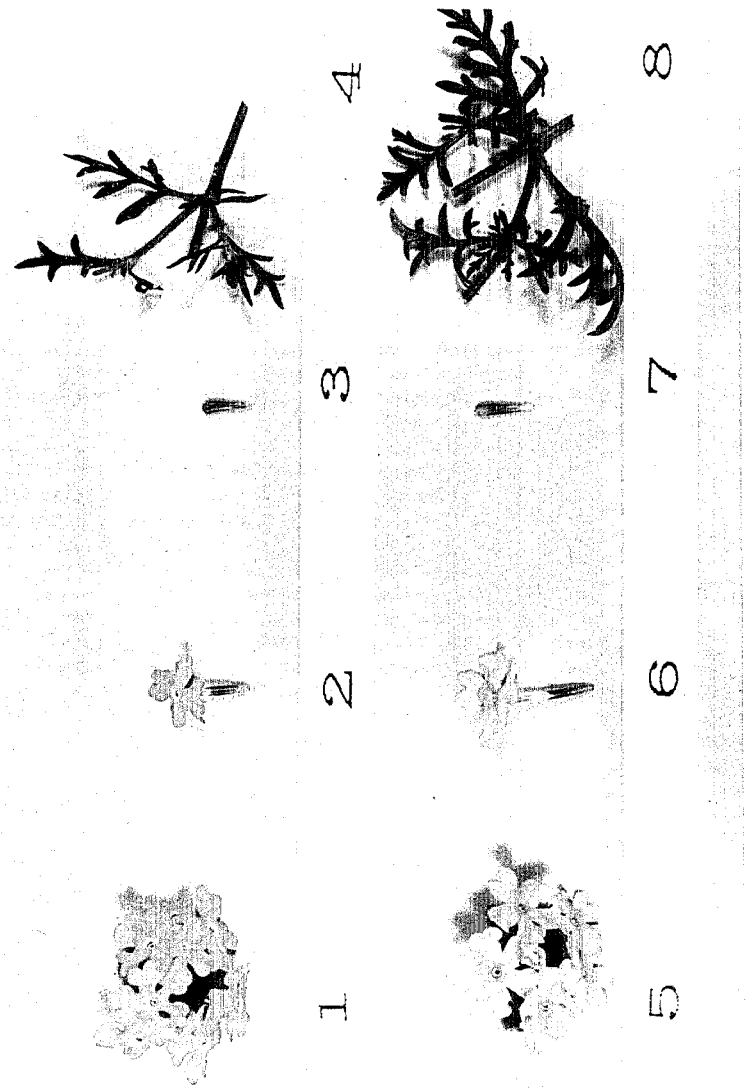
FIG. 4 is a photograph showing, in numerical order, a cluster (1), a flower (2), a bud (3), and a branch (4) of a similar variety 'Rainbowcarpet Rose', in comparison with corresponding items (5–8) of the new variety of verbena plant.

The botanical characteristics of the new and distinct variety of verbena plant, 'Sunmaref TP-P' are as follows.

Plant:

*Growth habit.*—Spreading.

*Plant height.*—20–25 cm.

*Spreading area of plant.*—The stem extends to a length of 40–50 cm, with semi-upward portion at the end, and thus the spreading area of the plant is 80–100 cm.

*Growth.*—Very vigorous with abundant branching and a great profusion of blooms; the whole bush remaining in bloom for a considerable period of time.

*Blooming period.*—Late April to November, in all areas of Japan.

*Ploidy.*—Normal.

Stem:

*Diameter.*—2–3 mm.

*Anthocyanin pigmentation.*—Absent.

*Branching.*—Abundant; with each node contacting the ground commonly forms deep-spreading roots.

*Length of internode.*—40–50 mm.

*Pubescence.*—Medium.

Leaf:

*Phyllotaxis.*—Opposite.

*Shape of blade.*—Progressively cut deeply into the branches in 2 to 3, or more stages.

*Length.*—20–25 mm.

*Width.*—30–35 mm.

*Depth of incision.*—Deep.

*Color.*—Moderate yellow green (R.H.S. 137C, J.H.S. 3712).

*Pubescence.*—Some pubescence commonly is present.

*Stipules.*—Absent.

Flower:

*Direction.*—Upward.

*Outward curvatuve of petal.*—Slightly curved.

*Diameter.*—12–15 mm.

*Length.*—12–15 mm.

*Cluster.*—Umbel; formed from 10 flowers.

*Color.*—Deep purplish pink (R.H.S. 61D, 66C, J.H.S. 9505), with eye color which is a deeper purplish red (R.H.S. 58B, J.H.S. 9706). The coloration generally does not fade upon exposure to sunlight.

*Color intensity.*—Present.

*Overlapping of petals.*—Separate.

*Spike.*—20–25 mm in length; and 35–40 mm in diameter.

*Calyx.*—1.3–1.5 cm in length. It is typical for the genus.

*Anthocyanin pigmentation of calyx limb.*—Generally present in no particular pattern.

*Peduncle.*—2–3 mm in thickness; and 6.0–8.0 cm in length.

*Number of flowers.*—Abundant (10±2).

*Reproductive organs.*—1 pistil and 5 stamens. Seeds commonly are formed in a very low frequency.

Physiological and ecological characteristics: High tolerances to cold and heat. The new variety is a perennial and has satisfactorily withstood temperatures as low as 0° C. and as high as 35° C. when grown in the field at Osaka, Japan. Also strong resistances to pests and diseases, particularly powdery mildew. The pinching of spent spikes commonly is necessary for a continuation of blossom production. Thinning is not required to maintain the new variety.

This new variety of verbena plant is most suitable for flower bedding and potting, particularly in planters, and is further excellent for ground cover. The new variety grows well in full sun, and has no particular fertilizer requirement for good performance. The plant also grows well in the shade, but commonly does not bloom well in the absence of sunlight.

The plant of this new variety, 'Sunmaref TP-P' is presently planted and maintained at the Plant Biotechnology Laboratory, Institute for Fundamental Research of SUNTORY Ltd., residing at 2913-1 Torihara, Hakushu-cho, Kitakoma-gun, Yamanashi-ken, Japan.

We claim:

1. A new distinct variety of verbena plant, substantially as herein illustrated and described, characterized particularly as to novelty by (A) a spreading growth habit with long stems, (B) the formation of abundant branching with each node of said spreading branches that contacts the ground commonly forming deep-spreading roots, (C) the formation of many flowers in ascending spikes to create a great profusion of blooms, (D) the formation of flowers that have petals having a deep purplish pink coloration with a small purplish red eye of deeper coloration, and (E) a high resistance to heat, cold, rain, diseases, and pests.

* * * * *